US005582975A

United States Patent [19]
Milliman

[11] Patent Number: 5,582,975
[45] Date of Patent: *Dec. 10, 1996

[54] NUCLEIC ACID PROBES TO STAPHYLOCOCCUS AUREUS

[75] Inventor: Curt L. Milliman, St. Louis, Mo.

[73] Assignee: Gen-Probe Incorporated, San Diego, Calif.

[ * ] Notice: The term of this patent shall not extend beyond the expiration date of Pat. No. 5,292,874.

[21] Appl. No.: 178,454

[22] Filed: Jan. 6, 1994

Related U.S. Application Data

[63] Continuation of Ser. No. 753,362, Sep. 4, 1991, Pat. No. 5,292,874.

[51] Int. Cl.$^6$ .............................. C12Q 1/68; C12P 19/34; C07H 21/04; C12N 15/00
[52] U.S. Cl. ......................... 435/6; 435/91.1; 435/91.2; 435/882; 435/883; 536/23.7; 536/24.3; 536/24.32; 935/8; 935/77; 935/78
[58] Field of Search .............................. 435/6, 883, 91.1, 435/91.2; 536/23.7, 24.3, 24.32, 24.33; 935/8, 77, 76, 78; 436/94, 882, 883, 884, 183

[56] References Cited

U.S. PATENT DOCUMENTS

| | | |
|---|---|---|
| 4,689,295 | 8/1987 | Taber et al. . |
| 5,292,874 | 3/1994 | Milliman .............................. 536/24.32 |

FOREIGN PATENT DOCUMENTS

| | | |
|---|---|---|
| 3138784 | 8/1984 | Australia . |
| 0155359 | 9/1985 | European Pat. Off. . |
| 0232085 | 8/1987 | European Pat. Off. . |
| 0245129 | 11/1987 | European Pat. Off. . |
| 0250662 | 1/1988 | European Pat. Off. . |
| 0277237 | 8/1988 | European Pat. Off. . |
| 0301073 | 3/1983 | WIPO . |
| 8402721 | 7/1984 | WIPO . |
| 8803957 | 2/1988 | WIPO . |

OTHER PUBLICATIONS

*Bergy's Manual of Systematic Bacteriology* 1:L160 (1984).
*Bergy's Manual of Systematic Bacteriology*, p. 283 (1984).
Brenner, "Deoxyribonucleic Acid Reassociation in the Taxonomy of Enteric Bacteria," *International Journal of Systematic Bacteriology* 23:298 307 (1973).
Brenner, "DNA Hybridization for Characterization, Classification, and Identification of Bacteria," in *Nucleic Acid and Monoclonal Antibody Probes*, ed. Bala Swaminathan (New York:Marcel Dekker, Inc. 1989 pp. 75–104.
Brenner, "Facultatively Anaerobic Gram–Negative Rods," from *Bergy's Manual of Systematic Bacteriology* 1:408–410 (1984).
Brenner et al., "Ten News Species of *Legionella*," *International Journal of Systematic Bacteriology* 35:50–59 (1985).
Brenner et al., "DNA percent relatedness among *Legionellae*–Table 4—from Family *Legionellaceae*", *International Journal Systematic Bacteriology* 30:236 (1980).

Brenner et al., "Classification of the Legionnaires' Disease Bacterium: An Interim Report," *Current Microbiology* 1:71–75 (1978).
Brenner et al., "Classification of the Legionnaires' Disease Bacterium: *Legionella pneumophila*, genus novum, species nova, of the Family Legionellaceae, familia nova," *Annals of Internal Medicine* 90:656–658 (1979).
Brosius et al., "Complete nucleotide sequence of a 23S ribosomal RNA gene from *Excherichia coli*," *Proc. Natl. Acad. Sci. USA* 77:201–204 (1980).
Brosius et al., "Complete nucleotide sequence of a 16S ribosomal RNA gene from *Excherichia coli*," *Proc. Natl. Acad. Sci. USA* 75:4801–4805 (1978).
Carbon et al., "The sequence of the ribosomall 16S RNA from *Protcus vulgaris*," *Nucleic Acids Research* 9:23325–2333 (1981).
*Clinical Microbiology Newsletter* 9:90–91 (1987).
Colwell et al., "Numerical Taxonomy and Deoxyribonucleic Acid Reassociation in the Taxonomy of Some Gram–Negative Fermentative Bacteria," *International Journal of Systematic Bacteriology* 24:422–433 (1974).
Crosa et al., "Polynucleotide Sequence Divergence in the Genus *Citrobacter*," *Journal of General Microbiology* 83:271–282 (1974).
Festl et al., "DNA hybridization Probe for the *Pseudomonas fluorescens* Group," *Applied and Enviromental Microbiology* 52:1190–1194 (1986).
Goering and Duensing, J. Clin Microbiol. 28:456–429 (1990).
Grimont et al., "DNA Probe Specific for *Legionella pneumophila*," *J. Clin. Microbiol.* 21:431–437 (1985).
Klipper–Bälz and Schleifer, "DNA–rRNA Hybridization Studies Among *Staphylococci* And Some Other Gram–Positive Bacteria," *FEMS Microbiology Letters* 10:357–362 (1981).
Klipper–Bälz et al., "Nucleic Acid Hybridization of Group N and Group D streptococci," *current microbilogy* 7:245–250 (1982).
Kohne, "Application of DNA probe tests to the diagnosis of infectious disease," *American Clinical Products Review*, Nov. (1986).
Kohne et al., "Nucleic Acid Probe Specific for Members of the Genus *Legionella*," in *Proceedings of the Second International Symposium American Society for Microbiology*, C. Thornsbury, A. Balows, J. C. Freeley, and W. Jakukowski eds. (Washington D.C.) pp. 107–108.
Lane et al., "Rapid determination of 16S ribosomal RNA sequences for phylogenetic analyses," *Proc. Natl. Acad. Sci. USA* 82:6955–6959 (1985).
Ludwig and Stackebrandt, "A phylogenetic analysis of *Legionella*," *Archives of Microbiology* 135:45–50 (1983).

(List continued on next page.)

Primary Examiner—W. Gary Jones
Assistant Examiner—Bradley L. Sisson
Attorney, Agent, or Firm—Lyon & Lyon

[57] ABSTRACT

Hybridization assay probes specific for *Staphylococcus aureus* and no other Staphylococcus species.

22 Claims, No Drawings

OTHER PUBLICATIONS

McCarroll et al, "Nucleotide Sequences of the *Dictyostelium discoideum* Small–Subunit Ribosomal Ribonucleic Acid inferred from the Gene Sequence: Evolutionary Implications," *Biochemistry* 23:5858–5868 (1983).

Razin, *Microbiol. Rev.* 49:437 (1985).

Rogers et al., "Construction of the mycoplasma evolutionary tree from 5S rRNA sequence data," *Proc. Natl. Acad. Sci. USA* 82:1160–1164 (1985).

Stahl, "Evolution, Ecology, and Diagnosis: Unity in Variety," *Biotechnology* 4:623–628 (1986).

Veldman et al., "The primary and secondary structure of yeast 26S rRNA," *Nucleic Acids Research* 9:6935–6953 (1981).

Weisburg et al., "Eubacterial Origin of *Chlamydiae*," *Journal of Bacteriology* 167:570–574 (1986).

Baess, "Deoxyribonucleic Acid Relationships Between Different Serovars of *Mycobacterium avium, Mycobacterium intracellulare* and *Mycobacteriaum scrofulaceum*," *Acta. Path. Microbiol. Immunol Scand. Sect B.* 91:201–203 (1983).

Baess, "Deoxyribonucleic Acid Relatedness Among Species of Rapidly Growing Mycobacteria," Acta. Path. Microbiol. Immunol. Scand Sect B. 90:371–375 (1982).

Baess and Bentzon, "Deoxyribonucleic Acid Hybridization Between Different Species of Mycobacteria," *Acta. Path. Microbiol. Scand Sect. B* 86:71–76 (1978).

Boddinghaus et al., "Detection and Identification of Mycobacteria by Amplification of rRNA," *J. Clinical Microbiology* 28:1751–1759 (1990).

Bradley, "Relationships Among Mycobacteria and Narcardiae Based upon Deoxyribonucleic Acid Reassociation," *J. Bacteriology* 113:645=14 651 (1973).

Drake et al., "Rapid Identification of *Mycobacterium avium* complex in Culture Using DNA Probes," *J. Clinical Microbiology* 25:1442–1445 (1987).

Göbel and Stanbridge, "Cloned Mycoplasm Ribosomal RNA Genes for the Detection of Mycoplasma Contamination in Tissue Cultures," *Science* 226:1211–1213 (1984).

Göbel et al "Oligonucleotide Probes Complementary to Variable Regions of Ribosomal RNA Discriminate between *Mycoplasma* Species," *Journal of General Microbiology* 133:1969–1974 (1987).

Goodfellow and Minnikin, "Circumscription of the Genus," *The Mycobacteria*, pp. 1–24, Kubica and Wayne eds. (Dekker; New York, 1984).

Goodfellow and Wayne in *The Biology of the Mycobacteria* Ralledge & Stanford eds. (Acad Press 1982).

Harvey and Greenwood, "Relationships Among Catalase–Positive Campylobacters Determined by Deoxyribonucleic Acid–Deoxyribonucleic Acid Hybridization," *International Journal of Systematic Bacteriology* 33:275–284 (1983).

Imaeda, "Deoxyribonucleic Acid Relatedness Among Selected Strains of *Mycobacterium tuberculosis, Mycobacterium bovis, Mycobacterium bovis BCG, Mycobacterium microti,* and *Mycobacterium africanum*," *International Journal of Systematic Bacteriology* 35:147–150. (1965).

Jones and Collins,, "Irregular, Nonsporing Gram–Positive Rods," *Bergy's Manual of Systematic Bacteriology* 2:1261–1266 (1986).

Killian, "A Taxonomic Study of the Genus Haemophilus, with the Proposal of a New Species," *J. General Microbilogy* 93:9–62 (1976).

Lau et al., "Phylogenetic Diversity and Position of the Genus *Campylobacter,*" *System App. Microbiol.* 9:231–258 (1987).

Malouin et al., "DNA Probe Technology for Rapid Detection of *Haemophilus influenzae* in Clinical Specimens," *J. Clin. Microbiology* 26:2132–2138 (1988).

Monzon–Moreno et al., "Usefulness of three probes in typing isolates of methicillin resistant *Staphylococcus aureus* (MRSA)" *J. Med. Microbiol.* 35:80–88 (1991).

Mordarski et al., "Ribosomal Ribonucleic Acid Similarities in the Classification of *Rhodococcus* and Related Taxa," *Journal of General Microbiology* 118:313–319 (1980).

Musser et al., "Genetic Relationships of Serologically Nontypable and Serotype b Strains of *Haemophilum influenzae,*" *Infection and Immunity* 52:183–191 (1986).

Razin, "Molecular Biological and Genetics of Mycoplasmas (Mollicutes)," *Microbiol. Rev.* 49:419–455 (1985).

Razin et al., "Molecular and Biological Features of Mollicules (Mycoplasmas)", *Ann. Microbiol.* 135:9–15 (1984).

Rogall et al., "Towards a Phylogeny and Definition of Species at the Molecular Level within the Genus *Mycobactyerium,*" *International Journal of Systematic Bacteriology* 40:323–330 (1990).

Rogall et al., "Differentiation of *Mycobacterium* Species by dfirect sequencing of amplified DNA," J. Gen. Microbiology 136:1915–1920 (1990).

Schleifer and Klipper–Balz, "Transfer of *Streptococcus faecalis* and *Streptococcus faecium* to the Genus *Enterococcus* nom. rev. as *Enterococcus faecalis* comb. nov. and *Enterococcus faecium* cobm. nov.," *Int'l. J. System. Bact.* 34:31–34 (1984).

Stackebrandt and Schleifer, "Molecular Systematics of Actinomycetes and Related Organisms," *Biological, Biochemical and Biomedical aspects of Actinomycetes* pp. 485–504 (1984).

Yogev and Razin, "Common Deoxyribonucleic Acid Sequences in *Mycoplasma genitalium* and *Mycoplasma pneumoniae* Genomes," Int'l J. System. Bacter. 36:426–430 (1986).

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CCACTCAAGA GAGACAACAT TTTCGACTAC    30

( 2 ) INFORMATION FOR SEQ ID NO: 2:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GATGATTCGT CTAATGTCGA CCTTTGTAAC TCC    33

( 2 ) INFORMATION FOR SEQ ID NO: 3:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CGGAATTTCA CGTGCTCCGT CGTACTCAGG AT        32

( 2 ) INFORMATION FOR SEQ ID NO: 4:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GTAGTCGAAA ATGTTGTCTC TCTTGAGTGG        30

( 2 ) INFORMATION FOR SEQ ID NO: 5:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GUAGUCGAAA AUGUUGUCUC UCUUGAGUGG        30

( 2 ) INFORMATION FOR SEQ ID NO: 6:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CCACUCAAGA GAGACAACAU UUUCGACUAC        30

NUCLEIC ACID PROBES TO *STAPHYLOCOCCUS AUREUS*

This is a continuation of application Ser. No. 07/753,362, filed Sep. 4, 1991 U.S. Pat. No. 5,292,874.

FIELD OF THE INVENTION

The inventions described and claimed herein relate to the design and construction of nucleic acid probes to *Staphylococcus aureus* which are capable of detecting the organism in test samples of, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851, 330, and Hogan et al., EPO Patent Application No. PCT/US87/03009, entitled "Nucleic Acid Probes for Detection and/or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium, Mycobacterium intracellulare, Mycobacterium tuberculosis, Mycobacterium africanum, Mycobacterium bovis, Mycobacterium microti,* the genus Mycobacterium, *Mycoplasma pneumoniae,* the genus Legionella, *Chlamydia trachomatis,* the genus Campylobacter, Enterococcus, the genus Pseudomonas group I, *Enterobacter cloacae, Proteus mirabilis,* the genus Salmonella, *Escherichia coli,* bacteria, fungi, and *Neisseria gonorrhoea.* Such probe sequences do not cross react with nucleic acids from the groups listed above, or any other bacterial species or infectious agent, under appropriate hybridization stringency conditions.

SUMMARY OF THE INVENTION

*Staphylococcus aureus* is the causative agent of a wide variety of infections in humans, including diseases of the skin and soft tissues. e.g., skin pustules, impetigo, bacteremia, osteomyelitis, renal abscess, pneumonia, meningitis, endocarditis, gastroenteritis and toxic shock syndrome (Kloos and Schleifer, Staphylococcus, In Bergey's Manual of Systematic Bacteriology, 1013–1019, 1986). Further, *S. aureus* is a prominent agent of nosocomial infections. Methicillin resistant strains (MRSA) have emerged as a major epidemiological problem in hospitals throughout the United States.

Within the genus Staphylococcus, *S.aureus* is the most clinically significant species due to the incidence and severity of the infections it can cause (Morse, Stapylococci, in Medical Microbiology and Infectious Diseases. Abraham Braude, editor, W. B. Saunders Company, Philadephia, Pa., 1981).

Current methods used to identify *Staphylococcus aureus* include Gram Stain morphology, cell morphology, production of catalase, pigment production, susceptibility to lysostaphin and lysozyme and anaerobic production of acid from glucose (Kloos and Schleifer, Simplified Scheme for Routine Identification of Human Staphylococcus Species, 1J. Clin. Microbiol. 82, 1975). In addition, there are several commercially available systems that allow strains to be biochemically characterized.

Among Staphylococcus species associated with human infections, *S. aureus* is unique in its ability to clot plasma (coagulase). It should be noted, however, that some Staphylococcus species found in animals, such as *S. intermedius* and *S. hyicus* may also share this property. Two different coagulase tests are commonly used to identify *S. aureus*. One is a tube test for free coagulase, and the other is a slide test for bound coagulase. The tube coagulase test is thought be be the more definitive of the two, however it can take several hours, or even an overnight incubation period to produce a result. Using the slide coagulase test, up to 10 to 15 percent of *S. aureus* stains may yield a negative result (Jorgeuen and Kloos, Staphylococcal Infections, Diagnostic Procedures for Bacterial Infections, 7th ed. B. B. Wentworth. American Public Health Association, Washington, DC 1987). Because of the existence of problem clinical isolates that may not be identified using current methods, and because of the coagulase-positive strains associated with animals, an alternative identification method is needed.

Thus, in a first aspect, the invention features a hybridization assay probe able to distinguish *Staphylococcus aureus* from other Staphylococcus species.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Staphylococcus aureus;* the probe is a nucleotide polymer able to hybridize to the rRNA of the species *Staphylococcus aureus* in the region corresponding to bases 338–367 of *E. coli* 23S rRNA, or a nucleotide polymer complementary thereto; and the oligonucleotide comprises, consists essentially of, or consists of the sequence (SEQ. ID. NO.: 1) CCACTCAAGAGAGACAACATTTTCGACTAC or oligonucleotides complementary thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides, and a nucleic acid sequence substantially complementary thereto.

The probes of this invention offer a rapid, non-subjective method of identification and quantitation of a bacterial colony for the presence of specific rRNA sequences unique to all strains of *Staphylococcus aureus*.

Other features and advantages of the invention will be apparent from the following description of the preferred embodiments thereof, and from the claims.

DESCRIPTION OF THE PREFERRED EMBODIMENTS

Probes

We have discovered DNA probes complementary to a particular rRNA sequence obtained from *Staphylococcus aureus*. Furthermore, we have successfully used those probes in a specific assay for the detection of *Staphylococcus aureus*, distinguishing *S. aureus* from its known and presumably most closely related taxonomic or phylogenetic neighbors.

With the exception of viruses, all prokaryotic organisms contain rRNA genes encoding 5S rRNA, 16S rRNA and a larger rRNA molecule known as 23S rRNA. Using methods known to those skilled in the art, variable regions of rRNA sequences from the 23S rRNA of *Staphylococcus aureus* were identified as described below. Other such sequences can be identified using equivalent techniques. These methods include partially or fully sequencing the rRNA of *Staphylococcus aureus* and closely related phylogenetic neighbors, aligning the sequences to reveal areas of maximum homology, and examining the alignment for regions with sequence variation. The examples provided below are thus not limiting in this invention.

With respect to sequencing, complementary oligonucleotide primers of about 10–100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions were used to determine the nucleotide sequence of the extended product. Lane et al., 82 *Proc. Nat'l Acad. Sci. USA*, 6955, 1985. In a less preferred method, genomic ribosomal RNA sequences may also be determined by standard procedure.

It is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and % G and % C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, dimethyl sulfoxide (DMSO) and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. 2 J. Sambrook, E. F. Fritsch and T. Maniatis, *Molecular Cloning* 11 (2d ed. 1989).

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^{3}H$, $^{35}S$, $^{32}P$, $^{125}I$, $^{57}CO$ and $^{14}C$. Most methods of isotopic labelling involve the use of enzymes and include the known methods of nick translation, end labelling, second strand synthesis, and reverse transcription. When using radiolabelled probes, hybridization can be detected by autoradiography, scintillation counting, or gamma counting. The detection method selected will depend upon the hybridization conditions and the particular radio-isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed. 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990, entitled "Homogeneous Protection Assay," assigned to Gen-Probe Incorporated, Mar. 6, 1992, Reel/Frame 6057/0433-34, issued as U.S. Pat. No. 5,283,174 hereby incorporated by reference herein, also published under European Patent Application Publication Number 0 309 230, Mar. 29, 1989.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2–5 degree increments. This solution is then diluted with a mildly alkaline borate buffer and incubated at a lower temperature (for example 50° C.) for ten minutes.

Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. 2 J. Sambrook, E. F. Fritsch and T. Maniatis, *Molecular Cloning*, 9.51 (2d ed. 1989).

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. For example, 0.05 pmol of target is incubated with 0.012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0t_{1/2}$ is found graphically from the concentration corresponding to 50% of maximum hybridization-multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (U.S. Ser. No. 816, 711, entitled "Accelerated Nucleic Acid Reassociation Method," filed Jan. 7, 1986 abandoned in favor of U.S. Pat. No. 5,132,207, issued Jul. 21, 1992, hereby incorporated by reference herein), also published under European Patent Application Publication Number 0 229 442, Jul. 22, 1987, other methods of nucleic acid reassociation can be used.

The following example sets forth synthetic probes complementary to a unique rRNA sequence, or the corresponding gene, from a target organism, *Staphylococcus aureus*, and their use in a hybridization assay.

EXAMPLE

A probe specific for *S. aureus* was identified by sequencing with a primer complementary to the 23S rRNA. The following sequence was characterized and shown to be specific for *Staphylococcus aureus*, probe oligonucleotide SEQ. ID. No. 1: CCACTCAAGAGAGACAACATTTTC-GACTAC 3'. The phylogenetically near neighbors *S. saprophyticus*, *S. epidermidis* and *S. avium* and others were used as comparisons with the sequence of *S. aureus*.

This probe is 30 bases in length and hybridizes to the 23S rRNA of *S. aureus* corresponding to bases 338–367 of *E. coli*. To demonstrate the reactivity and specificity of the probe for *S. aureus*, it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes" filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold et al., 35 *Clin. Chem.* 1588, 1989.

Nucleic acid hybridization was enhanced by the use of "Helper Probes" as disclosed in Hogan et al., U.S. Pat. No. 5,030,557, entitled "Means and Methods for Enhancing Nucleic Acid Hybridization", allowed Dec. 17, 1990, and hereby incorporated by reference herein. RNA was hybridized to the acridinium ester-labeled probe in the presence of unlabeled Helper Probes, oligonucleotide SEQ. ID. NO. 2 with the sequence of 5' GATGATTCGTCTAATGTCGAC-CTTTGTAACTCC 3' and oligonucleotide SEQ. ID. NO. 3 with the sequence of 5' CGGAATTTCACGTGCTC-CGTCGTACTCAGGAT 3'.

In the following experiment, RNA released from one colony or $>10^8$ organisms was assayed. An example of such a method is provided by Murphy et al., U.S. Ser. No. 841,860, entitled "Method for Releasing RNA and DNA from Cells", filed Mar. 20, 1986, abandoned in favor of U.S. Ser. No. 298,765, filed Jan. 17, 1989, abandoned in favor of U.S. Ser. No. 711,114, filed Jun. 21, 1991, assigned to Gen-Probe Incorporated, May 23, 1986, Reel/Frame 4566/0901, which issued as U.S. Pat. No. 5,374,522 hereby incorporated by reference herein, also published under European Patent Application Publication Number 0 288 618, Feb. 11, 1988. An RLU value greater than 30,000 RLU is a positive reaction; less than 30,000 is a negative reaction.

The following data show that the probe did not cross react with organisms from a wide phylogenetic cross section. These ATCC isolates were tested in duplicate, the RLU given is the average of the duplicates.

|    | ATCC # | Organism                    | RLU   | RESULT (+/−) |
|----|--------|------------------------------|-------|--------------|
| 1  | 33604  | *Acinetobacter calcoaceticus* | 5417  | −            |
| 2  | 15309  | *Acinetobacter lwoffii*       | 5336  | −            |
| 3  | 10049  | *Actinomyces israelii*        | 3327  | −            |
| 4  | 19411  | *Actinomyces Pyogenes*        | 3010  | −            |
| 5  | 11563  | *Aerococcus viridans*         | 2391  | −            |
| 6  | 7966   | *Aeromonas hydrophilia*       | 15644 | −            |
| 7  | 27061  | *Alcaligenes denitrificans*   | 1864  | −            |
| 8  | 8750   | *Alcaligenes faecalis*        | 3903  | −            |
| 9  | 6051   | *Bacillus subthis*            | 2510  | −            |
| 10 | 23745  | *Bacteroides fraclilis*       | 6085  | −            |
| 11 | 10580  | *Bordatella bronchisentica*   | 3452  | −            |
| 12 | 25238  | *Branhamella catarrhalis*     | 2790  | −            |
| 13 | 9172   | *Brevibacterium linens*       | 3714  | −            |
| 14 | 33560  | *Campylobacter jejuni*        | 4674  | −            |
| 15 | 18804  | *Candida albicans*            | 2796  | −            |
| 16 | 27872  | *Capnocytophacfa ochracea*    | 3020  | −            |
| 17 | 29094  | *Chromobacterium violaceum*   | 5819  | −            |
| 18 | 14501  | *Clostridium innocuum*        | 2161  | −            |
| 19 | 13124  | *Clostridium perfringens*     | 3393  | −            |
| 20 | 11913  | *Corynebacterium diphtheriae* | 3650  | −            |

| | ATCC # | Organism | RLU | RESULT (+/−) |
|---|---|---|---|---|
| 21 | 9345 | Corynebacterium haemolyticum | 2944 | − |
| 22 | 10700 | C. pseudodiphtheriticum | 2014 | − |
| 23 | 19410 | C. pseudotuberculosis | 2048 | − |
| 24 | 373 | Corynebacterium xerosis | 2070 | − |
| 25 | 32045 | Cryptococcus neoformans | 3134 | − |
| 26 | 35073 | Deinococcus radiodurans | 2991 | − |
| 27 | 15994 | Derxia gummosa | 2522 | − |
| 28 | 19433 | Enterococcus faecalis | 2520 | − |
| 29 | 19414 | Erysipelothrix rhusionathiae | 1732 | − |
| 30 | 10798 | Escherichia coli | 4607 | − |
| 31 | 13253 | Flavobacterium meningosepticum | 3941 | − |
| 32 | 10379 | Gemella haemolysans | 2804 | − |
| 33 | 19418 | Haemophilus influenzas | 3382 | − |
| 34 | 23357 | Klebsiella pneumonias | 5242 | − |
| 35 | 33152 | Legionella pneumophila | 6149 | − |
| 36 | 33313 | Leuconostoc paramesenteroides | 1912 | − |
| 37 | 35152 | Listeria monocytogenes | 2501 | − |
| 38 | 27570 | Micrococcus kristinae | 2059 | − |
| 39 | 4698 | Micrococcus luteus | 3150 | − |
| 40 | 27566 | Micrococcus lylae | 4628 | − |
| 41 | 186 | Micrococcus roseus | 2312 | − |
| 42 | 13077 | Neisseria meningitidis | 5834 | − |
| 43 | 19247 | Nocardia asteroides | 2209 | − |
| 44 | 33225 | Oerskovia turbata | 3278 | − |
| 45 | 27402 | Oerskovia xanthineolytica | 3024 | − |
| 46 | 17741 | Paracoccus denitrificans | 2032 | − |
| 47 | 33314 | Pediococcus acidilactici | 2813 | − |
| 48 | 14955 | Peptococgus magnus | 1420 | − |
| 49 | 27337 | Peptostreptococcus anaerobius | 3954 | − |
| 50 | 6919 | Propionibacterium acnes | 1944 | − |
| 51 | 25933 | Proteus mirabilis | 6970 | − |
| 52 | 25330 | Pseudomonas aeruginosa | 3075 | − |
| 53 | 33071 | Rahnella aquatilis | 2494 | − |
| 54 | 25592 | Rhodococcus bronchialis | 1516 | − |
| 55 | 33591 | Staphylococcus aureus | 658694 | + |
| 56 | 25904 | Staphylococcus aureus | 583913 | + |
| 57 | 12600 | Staphylococcus aureus | 543927 | + |
| 58 | 27660 | Staphylococcus aureus | 543617 | + |
| 59 | 12598 | Staphylococcus aureus | 542628 | + |
| 60 | 29213 | Staphylococcus aureus | 531156 | + |
| 61 | 29247 | Staphylococcus aureus | 527566 | + |
| 62 | 43866 | Staphylococcus aureus | 504506 | + |
| 63 | 12598 | Staphylococcus aureus | 472820 | + |
| 64 | 13301 | Staphylococcus aureus | 468886 | + |
| 65 | 33589 | Staphylococcus aureus | 463814 | + |
| 66 | 27661 | Staphylococcus aureus | 400398 | + |
| 67 | 25923 | Staphylococcus aureus | 299651 | + |
| 68 | 35662 | Staphylococcus cohnii | 3770 | − |
| 69 | 29887 | Staphylococcus epidermidis | 3294 | − |
| 70 | 14990 | Staphylococcus epidermidis | 2839 | − |
| 71 | 35983 | Staphylococcus epidermidis | 2658 | − |
| 72 | 12228 | Staphylococcus epidermidis | 2145 | − |
| 73 | 29970 | Staphylococcus haemolyticus | 2155 | − |
| 74 | 29885 | Staphylococcus hominis | 3716 | − |
| 75 | 29663 | Staphylococcus intermedium | 3769 | − |
| 76 | 43867 | Staphylococcus saprophyticus | 2959 | − |
| 77 | 15305 | Staphylococcus saprophyticus | 2665 | − |
| 78 | 11631 | Staphylococcus simulans | 10296 | − |
| 79 | 27836 | Staphylococcus warneri | 6348 | − |
| 80 | 13813 | Streptococcus agalactiae | 2509 | − |
| 81 | 9811 | Streptococcus mitis | 2028 | − |
| 82 | 6303 | Streptococcus pneumoniae | 2584 | − |
| 83 | 19615 | Streptococcus pyogenes | 6451 | − |
| 84 | 23345 | Streptomyces griseus | 4516 | − |
| 85 | 17802 | Vibrio parahaemolyticus | 6487 | − |
| 86 | 9610 | Yersinia entercolitica | 3211 | − |

The above data confirm that the novel probes herein disclosed and claimed are capable of distinguishing *Staphylococcus aureus* from its known nearest phylogenetic neighbors.

Other embodiments are within the following claims.

---

I claim:

1. An oligonucleotide hybridization assay probe able to detect the presence of *Staphylococcus aureus*, wherein said oligonucleotide has a length of 15 to 100 bases and can form a stable hybrid under high stringency conditions with a nucleotide polymer containing a nucleic acid base sequence selected from the group consisting of:

SEQ ID NO:
1 CCACTCAAGA GAGACAACAT TTTCGACTAC, and

SEQ ID NO: 5
GUAGUCGAAA AUGUUGUCUC UCUUGAGUGG;

wherein said oligonucleotide contains at least 14 out of 17 contiguous bases perfectly complementary to said nucleic acid sequence can hybridize to 23S rRNA or rDNA from *Staphylococcus aureus* under said conditions and under said conditions can distinguish *Staphylococcus aureus* nucleic acid from nucleic acid from *Staphylococcus cohnii, Staphylococcus epidermidis, Staphylococcus haemolyticus, Staphylococcus hominis, Staphylococcus intermedius, Staphylococcus saprophyticus, Staphylococcus simulans, Staphylococcus warneri, Staphylococcus agalactiae, Staphylococcus mitis, Staphylococcus pneumoniae, Staphylococcus pyogenes,* or *Staphylococcus griseus.*

2. The oligonucleotide of claim 1, wherein said oligonucleotide is 20 to 50 bases in length.

3. The oligonucleotide of claim 1, wherein said oligonucleotide contains a nucleotide base sequence selected from the group consisting of:

SEQ ID NO: 1 CCACTCAAGA GAGACAACAT TTTCGACTAC,

SEQ ID NO: 4 GTAGTCGAAA ATGTTGTCTC TCTTGAGTGG,

SEQ ID NO: 5 GUAGUCGAAA AUGUUGUCUC UCUUGAGUGG, and

SEQ ID NO: 6 CCACUCAAGA GAGACAACAU UUUCGACUAC.

4. The oligonucleotide of claim 3, wherein said oligonucleotide is 30 to 50 bases in length.

5. The oligonucleotide of claim 3, wherein said oligonucleotide consists of said nucleotide sequence.

6. The oligonucleotide of claim 5, wherein said oligonucleotide contains a detectable label selected from the group consisting of: radioisotope, fluorescent molecule, chemiluminescent molecule, enzyme, cofactor, enzyme substrate, and hapten.

7. The oligonucleotide of claim 6, wherein said detectable label is an acridinium ester.

8. A nucleic acid hybrid comprising:
   a) an oligonucleotide hybridization assay probe able to detect the presence of *Staphylococcus aureus*, wherein said oligonucleotide has a length of 15 to 100 bases and can form a stable hybrid under high stringency conditions with a nucleotide polymer containing a nucleic acid base sequence selected from the group consisting of:

SEQ ID NO: 1 CCACTCAAGA GAGACAACAT TTTCGACTAC, and

SEQ ID NO: 5 GUAGUCGAAA AUGUUGUCUC UCUUGAGUGG;

wherein said oligonucleotide contains at least 14 out of 17 contiguous bases perfectly complementary to said nucleic acid sequence, can hybridize to 23S rRNA or rDNA from *Staphylococcus aureus* under said conditions and under said conditions can distinguish *Staphylococcus aureus* nucleic acid from nucleic acid from *Staphylococcus cohnii, Staphylococcus epidermidis, Staphylococcus haemolyticus, Staphylococcus hominis, Staphylococcus intermedius, Staphylococcus saprophyticus, Staphylococcus simulans, Staphylococcus warneri, Staphylococcus agalactiae, Staphylococcus mitis, Staphylococcus pneumoniae, Staphylococcus pyogenes*, and *Staphylococcus griseus*; and
   b) a complementary nucleic acid sequence present in *Staphylococcus aureus* nucleic acid.

9. The hybrid of claim 8, wherein said oligonucleotide is 20 to 50 bases in length.

10. The hybrid of claim 9, wherein said oligonucleotide contains a nucleotide base sequence selected from the group consisting of:

SEQ ID NO: 1 CCACTCAAGA GAGACAACAT TTTCGACTAC,

SEQ ID NO: 4 GTAGTCGAAA ATGTTGTCTC TCTTGAGTGG,

SEQ ID NO: 5 GUAGUCGAAA AUGUUGUCUC UCUUGAGUGG, and

SEQ ID NO: 6 CCACUCAAGA GAGACAACAU UUUCGACUAC.

11. The hybrid of claim 10, wherein said oligonucleotide is 30 to 50 bases in length.

12. The hybrid of claim 10, wherein said oligonucleotide consists of said nucleotide sequence.

13. A method for determining whether *Staphylococcus aureus* is present in a sample comprising the steps of:
   a) contacting said sample under high stringency conditions with an oligonucleotide hybridization assay probe able to detect the presence of *Staphylococcus aureus*, wherein said oligonucleotide can form a stable hybrid under said conditions with a nucleotide polymer containing a nucleic acid base sequence selected from the group consisting of:

SEQ ID NO: 1 CCACTCAAGA GAGACAACAT TTTCGACTAC, and

SEQ ID NO: 5 GUAGUCGAAA AUGUUGUCUC UCUUGAGUGG;

wherein said oligonucleotide contains at least 14 out of 17 contiguous bases perfectly complementary to said nucleic acid sequence, can hybridize to 23S rRNA or rDNA from *Staphylococcus aureus* under said conditions and under said conditions can distinguish *Staphylococcus aureus* nucleic acid from nucleic acid from either *Staphylococcus cohnii, Staphylococcus epidermidis, Staphylococcus haemolyticus, Staphylococcus hominis, Staphylococcus intermedius, Staphylococcus saprophyticus, Staphylococcus simulans, Staphylococcus warneri, Staphylococcus agalactiae, Staphylococcus mitis, Staphylococcus pneumoniae, Staphylococcus pyogenes*, and *Staphylococcus griseus*; and
   b) detecting hybridization of said oligonucleotide to nucleic acid from *Staphylococcus aureus*.

14. The method of claim 13, wherein said oligonucleotide is 20 to 50 bases in length.

15. The method of claim 13, wherein said oligonucleotide contains a nucleotide base sequence selected from the group consisting of:

SEQ ID NO: 1 CCACTCAAGA GAGACAACAT TTTCGACTAC,

SEQ ID NO: 4 GTAGTCGAAA ATGTTGTCTC TCTTGAGTGG,

SEQ ID NO: 5 GUAGUCGAAA AUGUUGUCUC UCUUGAGUGG, and

SEQ ID NO: 6 CCACUCAAGA GAGACAACAU UUUCGACUAC.

16. The method of claim 15, wherein said oligonucleotide is 30 to 50 bases in length.

17. The method of claim 15, wherein said oligonucleotide consists of said nucleotide sequence.

18. A probe mix comprising:
   a) an oligonucleotide hybridization assay probe able to detect the presence of *Staphylococcus aureus*, wherein said oligonucleotide hybridization assay probe can form a stable hybrid under high stringency conditions with a nucleotide polymer containing a nucleic acid base sequence selected from the group consisting of:

SEQ ID NO: 1 CCACTCAAGA GAGACAACAT TTTCGACTAC, and

SEQ ID NO: 5 GUAGUCGAAA AUGUUGUCUC UCUUGAGUGG;

wherein said oligonucleotide hybridization assay probe contains at least 14 out of 17 contiguous bases perfectly complementary to said nucleic acid sequence, can hybridize to 23S rRNA or rDNA from *Staphylococcus aureus* under said conditions and under said conditions can distinguish *Staphylococcus aureus* nucleic acid from nucleic acid from *Staphylococcus cohnii, Staphylococcus epidermidis, Staphylococcus haemolyticus, Staphylococcus hominis, Staphylococcus intermedius,*

*Staphylococcus saprophyticus, Staphylococcus simulans, Staphylococcus warneri, Staphylococcus agalactiae, Staphylococcus mitis, Staphylococcus pneumoniae, Staphylococcus pyogenes,* and *Staphylococcus griseus;* and b) at least one helper probe oligonucleotide containing a helper probe nucleotide sequence selected from the group consisting of:

SEQ ID NO: 2

GATGATTCGT CTAATGTCGA CCTTTGTAAC TCC, and

SEQ ID NO: 3

CGGAATTTCA CGTGCTCCGT CGTACTCAGG AT.

19. The probe mix of claim 18, wherein said oligonucleotide hybridization assay probe is 20 to 50 bases in length.

20. The probe mix of claim 18, wherein said oligonucleotide hybridization assay probe is 20 to 50 bases in length and contains a hybridization assay probe nucleotide base sequence selected from the group consisting of:

SEQ ID NO: 1 CCACTCAAGA GAGACAACAT TTTCGACTAC,

SEQ ID NO: 4 GTAGTCGAAA ATGTTGTCTC TCTTGAGTGG,

SEQ ID NO: 5 GUAGUCGAAA AUGUUGUCUC UCUUGAGUGG, and

SEQ ID NO: 6 CCACUCAAGA GAGACAACAU UUUCGACUAC.

21. The probe mix of claim 20, wherein said oligonucleotide hybridization assay probe consists of said hybridization assay probe nucleotide sequence, and said at least one helper probe consists of said helper probe nucleotide sequence.

22. The probe mix of claim 21, wherein said at least one helper probe consists of a first helper probe of SEQ ID NO: 2 GATGATTCGT CTAATGTCGA CCTTTGTAAC TCC, and a second helper probe of SEQ ID NO: 3 CGGAATTTCA CGTGCTCCGT CGTACTCAGG AT.

* * * * *

UNITED STATES PATENT AND TRADEMARK OFFICE
CERTIFICATE OF CORRECTION

PATENT NO. : 5,582,975
DATED : Dec. 10, 1996
INVENTOR(S) : Curt L. Milliman

Page 1 of 2

It is certified that error appears in the above-identified patent and that said Letters Patent is hereby corrected as shown below:

Column 7, Line 42: Delete "$9.0 \times 10^-6$" and insert --$9.0 \times 10^{-6}$--

Column 8, Under the Heading "Organism", 9th entry down: Delete "*subthis*" and insert --*subtilis*--

Column 8, Under the Heading "Organism", 10th entry down: Delete "*fraclilis*" and insert --*fragilis*--

Column 8, Under the Heading "Organism", 11th entry down: Delete "*bronchisentica*" and insert --*bronchiseptica*--

Column 8, Under the Heading "Organism", 16th entry down: Delete "*Capnocytophacfa*" and insert --*Capnocytophaga*--

Column 9, Under the Heading "Organism", 15th entry down: Delete "*influenzas*" and insert --*influenzae*--

Column 9, Under the Heading "Organism", 16th entry down: Delete "*pneumonias*" and insert --*pneumoniae*--

Column 9, Under the Heading "Organism", 31st entry down: Delete "*Peptococgus*" and insert --*Peptococcus*--

Column 10, Under the Heading "Organism", 19th entry down: Delete "*intermedium*" and insert --*intermedius*--

UNITED STATES PATENT AND TRADEMARK OFFICE
CERTIFICATE OF CORRECTION

PATENT NO. : 5,582,975

DATED : December 10, 1996

INVENTOR(S) : Curt L. Milliman

It is certified that error appears in the above-identified patent and that said Letters Patent is hereby corrected as shown below:

Column 11, Line 60: After "sequence" insert --,--

Signed and Sealed this

Third Day of November, 1998

Attest:

Attesting Officer

BRUCE LEHMAN

Commissioner of Patents and Trademarks